(12) United States Patent
Johnson et al.

(10) Patent No.: US 8,822,549 B2
(45) Date of Patent: Sep. 2, 2014

(54) BUFFERED OXYGEN THERAPEUTIC

(76) Inventors: Jennifer L. Johnson, Tucson, AZ (US); Evan C. Unger, Tucson, AZ (US)

( * ) Notice: Subject to any disclaimer, the term of this patent is extended or adjusted under 35 U.S.C. 154(b) by 0 days.

(21) Appl. No.: 13/273,115

(22) Filed: Oct. 13, 2011

(65) Prior Publication Data
US 2013/0096204 A1    Apr. 18, 2013

(51) Int. Cl.
| | |
|---|---|
| *A61K 31/02* | (2006.01) |
| *A61K 31/7016* | (2006.01) |
| *A61K 47/26* | (2006.01) |
| *A61K 9/107* | (2006.01) |
| *A61K 31/685* | (2006.01) |
| *A61K 47/10* | (2006.01) |
| *A61K 31/03* | (2006.01) |
| *A61K 9/00* | (2006.01) |
| *A61K 31/025* | (2006.01) |

(52) U.S. Cl.
CPC ............. *A61K 9/0026* (2013.01); *A61K 31/685* (2013.01); *A61K 47/10* (2013.01); *A61K 31/02* (2013.01); *A61K 31/03* (2013.01); *A61K 31/7016* (2013.01); *A61K 47/26* (2013.01); *A61K 31/025* (2013.01)
USPC ................ 514/759; 514/53; 514/78; 514/738

(58) Field of Classification Search
CPC ..... A61K 31/02; A61K 47/26; A61K 31/685; A61K 9/107
See application file for complete search history.

(56) References Cited

U.S. PATENT DOCUMENTS

| | | | | |
|---|---|---|---|---|
| 4,423,077 A | * | 12/1983 | Sloviter | 514/759 |
| 5,114,932 A | * | 5/1992 | Runge | 514/58 |
| 5,558,853 A | | 9/1996 | Quay | |
| 7,357,937 B2 | * | 4/2008 | Hsu et al. | 424/400 |
| 2001/0023262 A1 | | 9/2001 | Raynolds et al. | |
| 2003/0032879 A1 | | 2/2003 | Quay | |
| 2004/0068020 A1 | | 4/2004 | Weers et al. | |
| 2005/0163716 A1 | * | 7/2005 | Unger et al. | 424/9.52 |
| 2010/0267842 A1 | | 10/2010 | Kiral et al. | |

OTHER PUBLICATIONS

Vercellotti et al. Blood, 1982, vol. 59, No. 6, pp. 1299-1304.*
Drug Future Chemical Data for Fluosol-DA (Accessed Aug. 19, 2013 from http://www.drugfuture.com/chemdata/fluosol-da.html).*
Johnson et al. Artificial Cells, Blood Substitutes, and Biotechnology, 2009, vol. 37, pp. 156-162.*
PCT/US2012/060284—International Search Report and Written Opinion dated Apr. 8, 2013.

* cited by examiner

*Primary Examiner* — James D Anderson
(74) *Attorney, Agent, or Firm* — Dale F. Regelman; Quarles & Brady LLP (57) ABSTRACT

An oxygen therapeutic composition, comprising a perfluorocarbon material, a viscosity modifier, a buffer, wherein the buffer stabilizes a pH of the composition at between about 6.5 to about 7.5, and wherein the composition comprises a viscosity of about 2.0 to about 3.5 mPas, and wherein the fluorocarbon has a boiling point of about 4 degrees Celsius to about 60 degrees Celsius.

6 Claims, 7 Drawing Sheets

BUFFERED OXYGEN THERAPEUTIC

TECHNICAL FIELD

The present invention relates to emulsions of perfluorinated materials useful as oxygen therapeutics.

BACKGROUND OF THE INVENTION

Because blood is prone to viral contamination, and because donated blood has a limited shelf life, donated blood appears to be in constant short supply. In response, much effort has been focused on the development of compositions commonly referred to as "blood substitutes" or "artificial blood". These compositions are appropriately termed "gas carriers".

Microbubbles have been developed for use as contrast-enhancing agents for ultrasonic imaging of the heart and blood vessels. Certain of these contrast-enhancing agent microbubbles are formed from PFCs and used in methods for ultrasound imaging. PFCs that are disclosed as being useful for creating microbubbles include dodecafluoropentane (DDFP).

BRIEF DESCRIPTION OF THE DRAWINGS

The invention will be better understood from a reading of the following detailed description taken in conjunction with the drawings in which like reference designators are used to designate like elements, and in which.

DETAILED DESCRIPTION OF SPECIFIC EMBODIMENTS

This invention is described in preferred embodiments in the following description with reference to the Figures, in which like numbers represent the same or similar elements. Reference throughout this specification to "one embodiment," "an embodiment," or similar language means that a particular feature, structure, or characteristic described in connection with the embodiment is included in at least one embodiment of the present invention. Thus, appearances of the phrases "in one embodiment," "in an embodiment," and similar language throughout this specification may, but do not necessarily, all refer to the same embodiment.

The described features, structures, or characteristics of the invention may be combined in any suitable manner in one or more embodiments. In the following description, numerous specific details are recited to provide a thorough understanding of embodiments of the invention. One skilled in the relevant art will recognize, however, that the invention may be practiced without one or more of the specific details, or with other methods, components, materials, and so forth. In other instances, well-known structures, materials, or operations are not shown or described in detail to avoid obscuring aspects of the invention.

This invention pertains to a surprising discovery pertinent to stabilizing an oxygen therapeutic which in turn is related to another surprising discovery that has already been described. Microbubbles transport far more oxygen (or other gases) per unit volume than other materials. Liquid perfluorocarbons have been studied extensively as blood replacements or as oxygen therapeutics. They have required high doses and have failed in clinical development. Gaseous fluorocarbons, in the form of microbubbles, however, require less than $1/100^{th}$ the dose of the liquid fluorocarbons to be effective as oxygen therapeutics.

Dodecafluoropentane ("DDFP") is a preferred microbubble forming agent for oxygen delivery. It forms an emulsion in water ("DDFPe") comprising sub-micron sized droplets at room temperature and converts to a gas at 29° C. To maintain the stability of the DDFPe emulsion Applicants have found that use of a viscosity modifying material prevents settling and agglomeration of the particles. Applicants have further discovered that sucrose is a preferred viscosity modifying material. This invention is directed towards the production of improved emulsions of oxygen therapeutics.

Dodecafluoropentane emulsion (DDFPe) contains a fluorocarbon, DDFP, in a sucrose solution. Applicants have found that addition of biologically accepted phosphate buffer at 0.01 M concentration into the sucrose solution prevents an acid-catalyzed/time-dependent breakdown of sucrose. The prevention of this chemical breakdown is important for the long-term physical stability of the NVX-108 (DDFPe) formulation for use as an oxygen therapeutic.

A buffer is provided that stabilizes the viscosity of the suspending medium surrounding an emulsion of a fluorocarbon material. The addition of a 0.01 M phosphate buffer to NVX-108, a dodecafluoropentane emulsion (DDFPe), stabilizes the pH. Applicants further discovered that this buffer actually functions to maintain the desired viscosity of the NVX-108 emulsion. Furthermore, the buffer prevents an increase in the osmotic concentration of the formulation over time. Due to its ability to organize in aqueous solution and form a quasi lattice-work to support the emulsion droplets, sucrose (30% w/v) is employed as the viscosity enhancer in this formulation. When a sucrose molecule hydrolyzes, it becomes a molecule of fructose and a molecule of glucose; thus, potentially doubling the overall solute concentration of the aqueous phase. In addition, fructose and glucose destabilize the sucrose scaffolding which in turn decreases the viscosity of NVX-108. Maintaining the integrity of the initial sucrose "structure" positively contributes to the physical stability of the formulation by maintaining a constant osmotic concentration, and the inherent molecular lattice that is specific to sucrose in water, to provide a 2-fold increase in viscosity.

Figure 1:
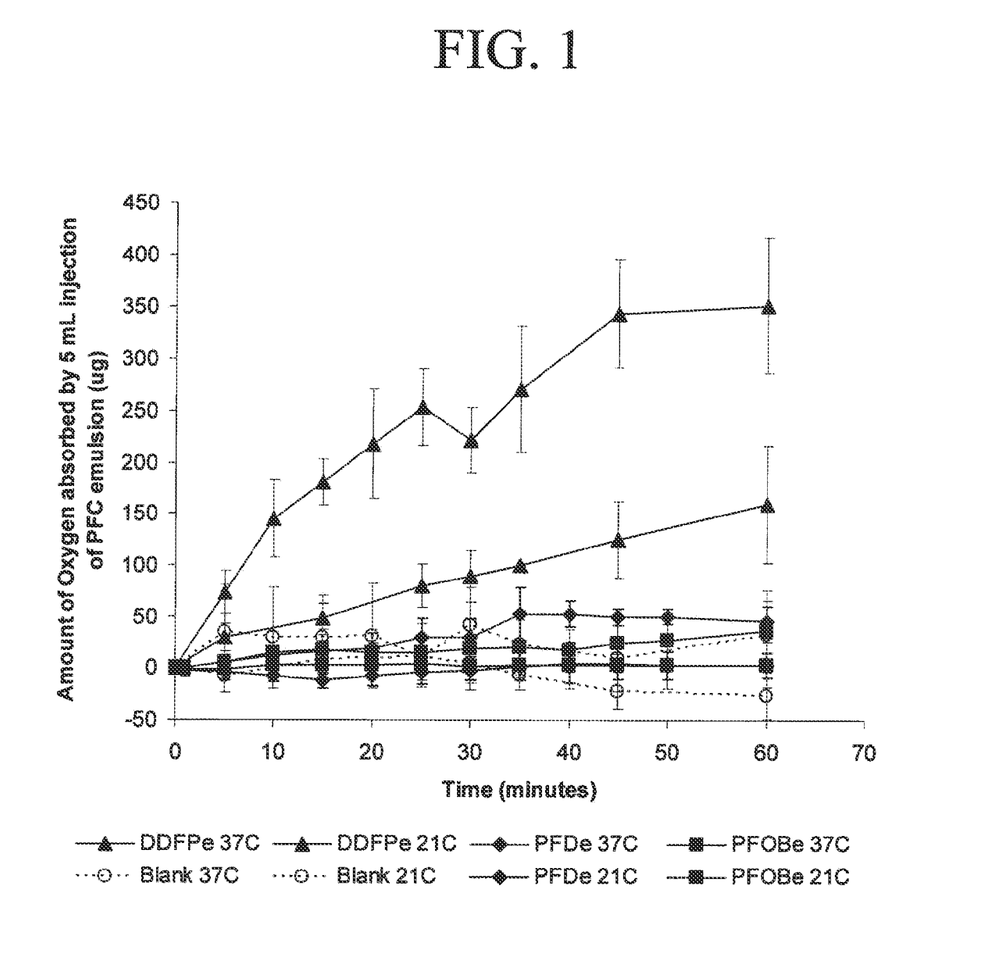
FIG. 1. is a graph of oxygen absorption of DDFPe and emulsions of perfluorodecalin and perfluoroctylbromide at room temperature and at physiologic temperature. DDFPe absorbs more oxygen at room temperature than the other agents and is even more effective at physiologic temperature (above the boiling point of DDFP)

Emulsions of DDFPe (as described below) and perfluoroctylbromide (PFOBe) and decafluoropentane (DFPe) were prepared (see description of production of DDFPe below. The ability of the different emulsions were compared as described in the published literature. The results are shown in FIG. 1.

The following example is presented to further illustrate to persons skilled in the art how to make and use the invention. This example is not intended as a limitation, however, upon the scope of the invention.

EXAMPLE I

A 32% sucrose solution was made, using high purity sucrose. A 0.01 M phosphate buffer was added to the solution in the form of equal molar parts of (0.005 M) $NaH_2PO_4$ and (0.005 M) $Na_2HPO_4$. The pH of the solution is then adjusted to the pKa of phosphate which is also physiologically compatible: pH=7.0-7.3. The sucrose solution was then used as the aqueous phase of the emulsion and is homogenized with the surfactant/DDFP mixture in the preparation of the DDFPe.

Sucrose samples of the formulation were analyzed using HPLC with a carbohydrate column (Zorbax, 4.6×150 mm, 5 um) suitable for providing separation of the sucrose from its potential degradation products, glucose and fructose. Viscosity of the formulations was assessed by cone and plate viscometry (Brookfield). The hydrogen ion concentration of the samples was measured using a pH probe and accompanying meter. A set of 5 standards of varying concentrations of sucrose, fructose and glucose appropriate to the concentrations expected in the samples were run by HPLC. The viscometer was calibrated to 1.0 mPas with pure water. The pH probe was calibrated using standard buffers of pH 4, 7 and 10.

In order to demonstrate the effect the pH has on the chemical stability of sucrose in DDFPe, the pH of 9 vials of buffered lot#021708 were intentionally adjusted down to pH 4 and stored at 25° C. for 37 days. The sucrose content of each of 3 separate vials was assayed at time points of 0, 10 and 37 days.

All instrument calibrations previously noted were followed by analysis of the following samples:
1) Buffered DDFPe:
   a. Three samples (3 vials) from 1 lot of phosphate buffered (0.01 M) DDFPe after 3 days of storage at 25° C. (lot#080611).
   b. Three samples (3 vials) from 1 lot of phosphate buffered (0.01 M) DDFPe after 3 years of storage at 25° C. (lot#021708).
2) Unbuffered DDFPe:
   a. Six samples (6 vials) from 2 lots of unbuffered DDFPe after 3 months of storage at 25° C. (lot#030806, #061207).
   b. Three samples (3 vials) from 1 lot of unbuffered DDFPe after 9 years of storage at 25° C. (lot#30-618-DK).

The HPLC method used for analysis is a gradient over 13 minutes of $ACN:H_2O$, which produces a chromatogram with well defined and well resolved peaks for fructose, glucose and sucrose. The viscometer and the pH meter were used according to their respective Users Manuals.

Microsoft Excel was used to graph standard curves of sugar concentration vs. area under the curve (AUC). The sugar levels of the samples were calculated according to these standard curves.

FIG. 1. graphically illustrates an amount of oxygen absorbed by emulsions of dodecafluoropentane (DDFPe), perfluorodecalin (PFDe) and perfluoroctylbromide (PFOBe). DDFPe outperforms the other perfluorocarbons at room temperature and is even much more effective at physiologic temperature which is greater than the boiling point of DDFP. These results are consistent with the theory that microbubbles are more effective at gas transport.

Table 1 shows comparative doses of fluorocarbons used in published studies as oxygen delivery agents. In these studies, fluorocarbons were administered systemically and oxygen was administered via inhalation to sensitize hypoxic tumors to radiation therapy. PFOB was effective at less than $\frac{1}{100}^{th}$ the dose of the liquid fluorocarbons fluosol and perfluoroctylbromide. These results again support the hypothesis that gaseous fluorocarbons are more effective for oxygen delivery than liquid fluorocarbons.

TABLE 1

Comparative Doses of Fluorocarbons as $O_2$ Delivery Agents

| Agent | DDFPe (1) | Fluosol (2) | PFOB (3) |
|---|---|---|---|
| Volume | 0.6 ml/kg | 8-9 ml/kg | 2-15 ml/kg |
| w/vol | 2% | 20% | 100% |
| g/kg | 0.012 g/kg | 1.6-1.8 g/kg | 2-15 g/kg |

Figure 2:
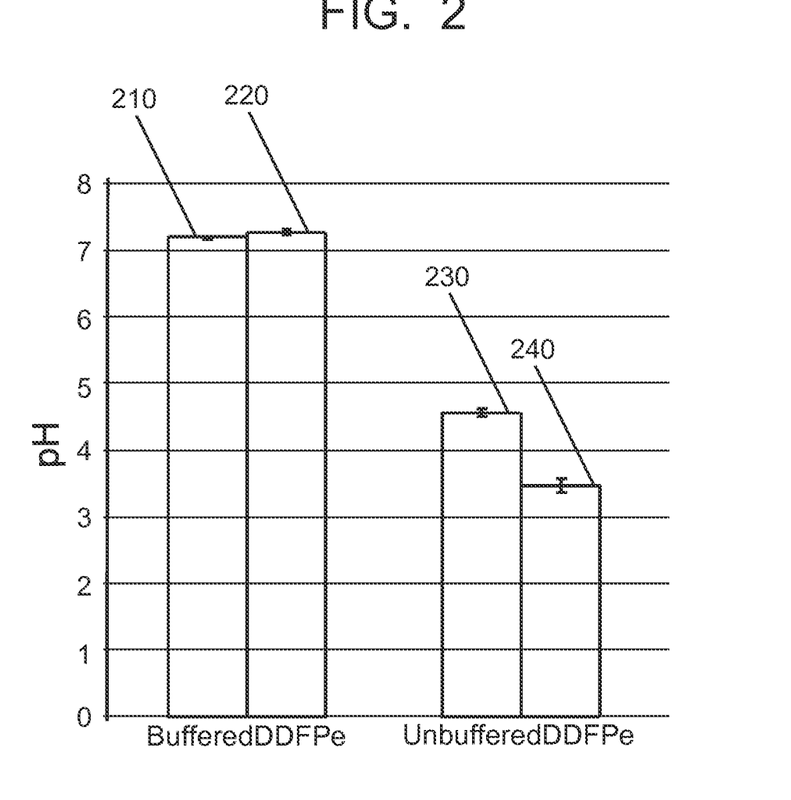
FIG. 2. is a comparison of pH values in DDFPe lots.

FIG. 2 graphically illustrates a comparison of pH values in DDFPe lots. Curves 210 and 220 show a 0.01 M phosphate buffered DDFPe lot#021708 at pH 7.2 before and after 3 years of storage at 25° C. Curves 210 and 220 are essentially identical. In contrast, curves 230 and 240 show the pH of an unbuffered DDFPe lot#030806 at 0 days storage and an unbuffered lot#39588DK02 after 9 years of storage at 25° C. Error bars represent ±1 standard deviation of triplicate samples.

The data recited in FIG. 2 show that the pH of DDFPe starts at about pH 4.5 to 5.5 and decreases with time. However, in combination with a pH buffer, the pH of DDFPe does not change over time.

Figure 3:
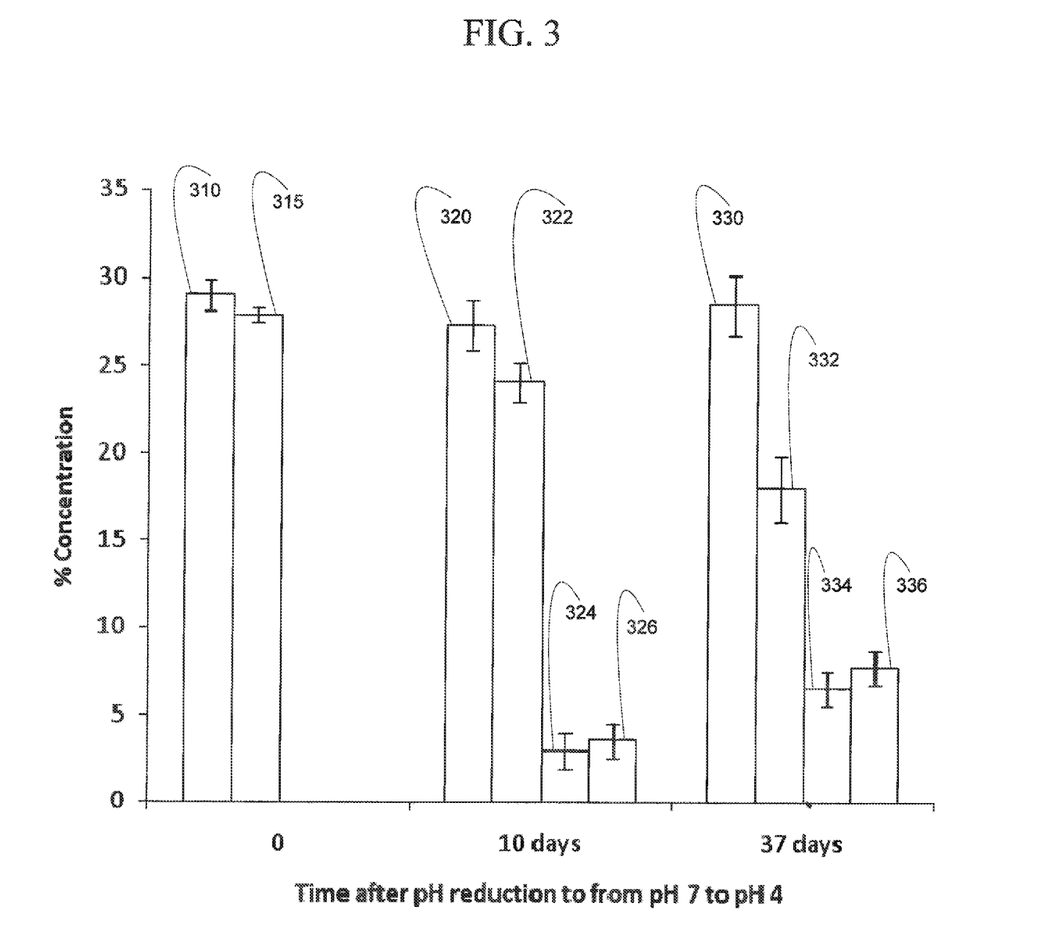
FIG. 3. is a comparison of sugar levels in DDFPe lots at pH 7.2 and at pH 4.0.

Acidic conditions promote the breakdown of the sucrose in DDFPe. FIG. 3 graphically shows a comparison of sugar levels in DDFPe lot#021708 at pH 7.2 and pH 4. Referring now to FIG. 3, curves 310, 320, and 330, show the concentration of sucrose in DDFPe buffered at pH 7.2 Error bars represent ±1 standard deviation. Curve 315 shows the concentration immediately after lowering the pH to about 4.0. Curve 322 shows the concentration of sucrose after 10 days at a pH of about 4.0. Curve 332 shows the concentration of sucrose after 37 days at a pH of about 4.0. Curves 324 and 334 show the concentration of fructose and curves 326 and 336 show the concentration of glucose.

Those skilled in the art will appreciate that sucrose I is a disaccharide formed from fructose II and glucose III.

Those skilled in the art will further appreciate that under acidic conditions, the acetal linkage in sucrose I joining the fructose moiety with the sucrose moiety can be cleaved to liberate fructose II and glucose III. FIG. 3 shows that as the sucrose concentration decreases, the concentrations of both fructose and glucose increase.

In cases where the pH of the DDFPe sucrose solution was adjusted up to pH 7.2 during preparation of the DDFPe/sucrose mixture, a lack of sucrose breakdown was observed, while lots of DDFPe that were unbuffered showed marked sucrose breakdown at 3 months after preparation. These data are exemplified in FIGS. 4, 5 and 6.

Figure 4:
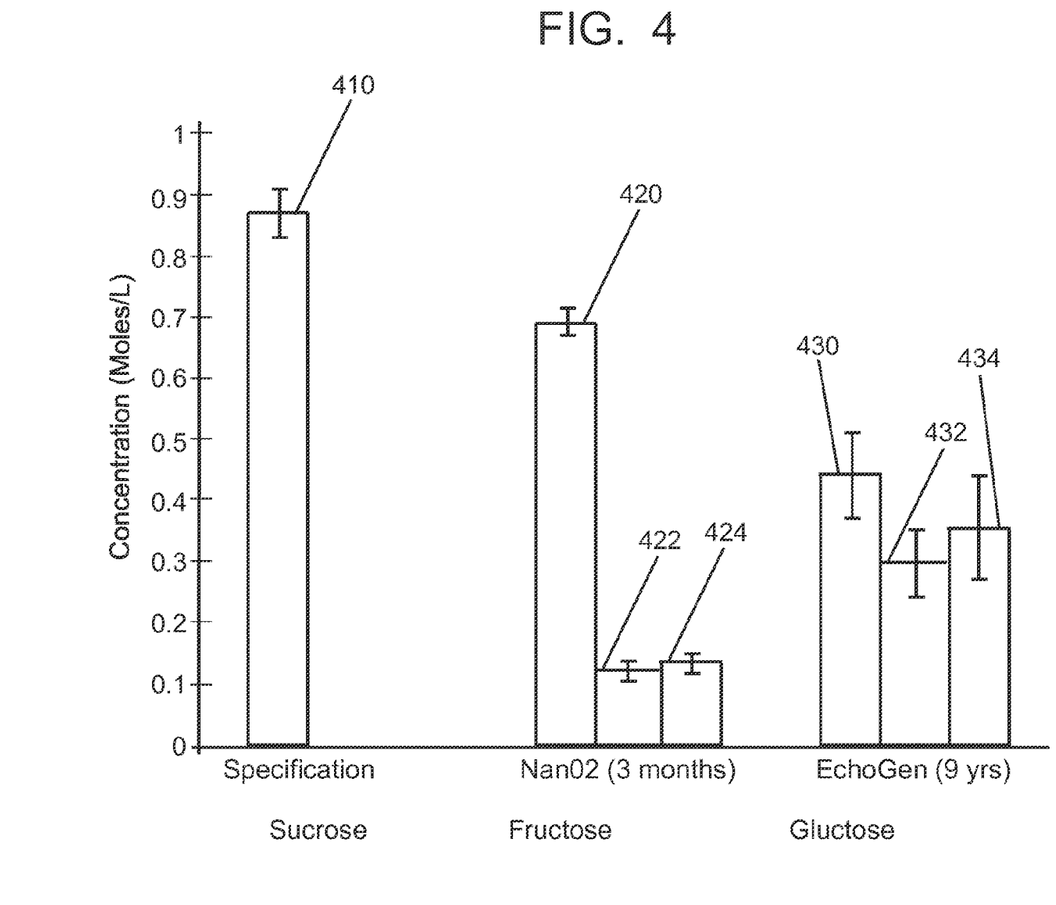
FIG. 4. is a comparison of sugar levels in DDFPe lots showing significant decrease in sucrose after only 3 months of storage of unbuffered material.
Figure 5A:
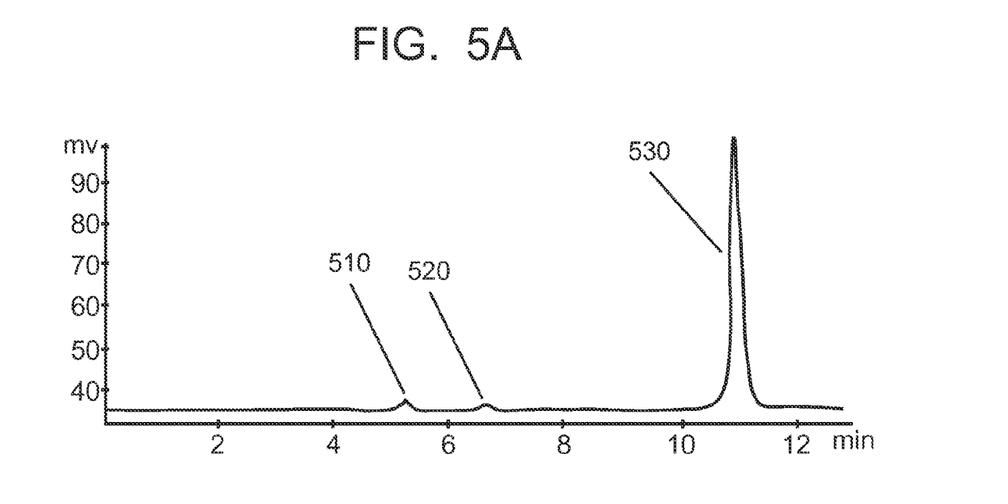
FIG. 5. shows sample chromatograms from HPLC analysis of 2 different lots of unbuffered DDFPe.
Figure 5B:
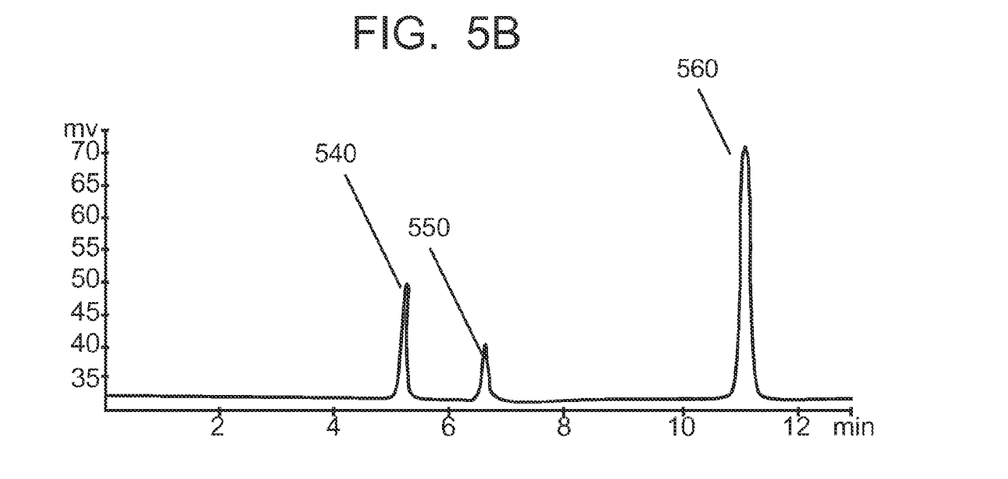

FIG. 4 shows the sugar levels assayed by HPLC of the same 2 lots shown in FIG. 5. Curve 410 shows the concentration of sucrose with no traces of either fructose and/or glucose in a buffered DDFPe/sucrose mixture. Curves 420, 422, and 424 shows the concentrations of sucrose, fructose, and glucose, in an unbuffered DDFPe/sucrose mixture after about 90 days. It also shows their comparison to the sugar levels of a buffered lot (#021708). The mixtures having the concentrations shown by curves 420/424/426 and 430/432/434 were stored under the same conditions albeit for different periods of time.

FIG. 5 shows the chromatograms of the 2 lots of unbuffered DDFPe of FIG. 4. Even at only 3 months of storage at room temperature (lot#030806), the breakdown of sucrose had begun. After 9 years (lot#39588DK02) the conversion of sucrose to fructose and glucose was more advanced. The buffered DDFPe/sucrose mixture corresponding to curve 410 in FIG. 4 showed no peaks for fructose or glucose.

Figure 6A:
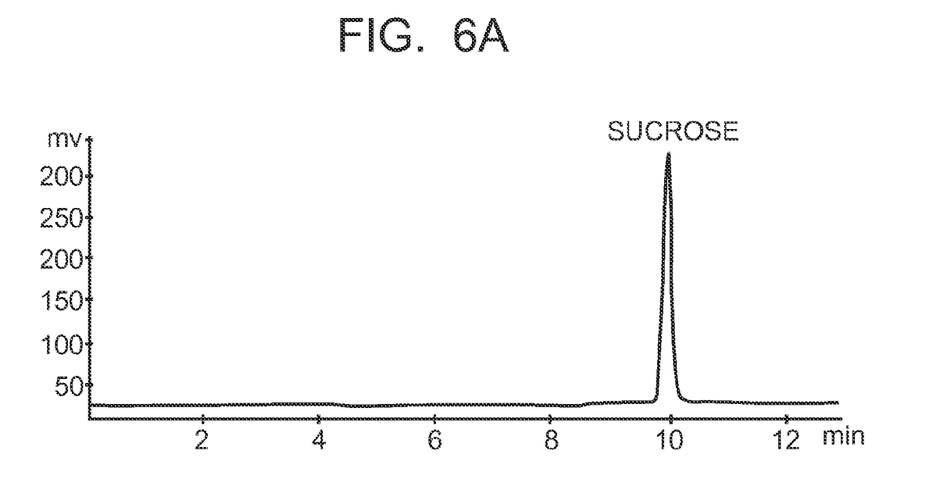
FIG. 6. shows sample chromatograms from HPLC analysis of 2 different lots of buffered DDFPe.
Figure 6B:
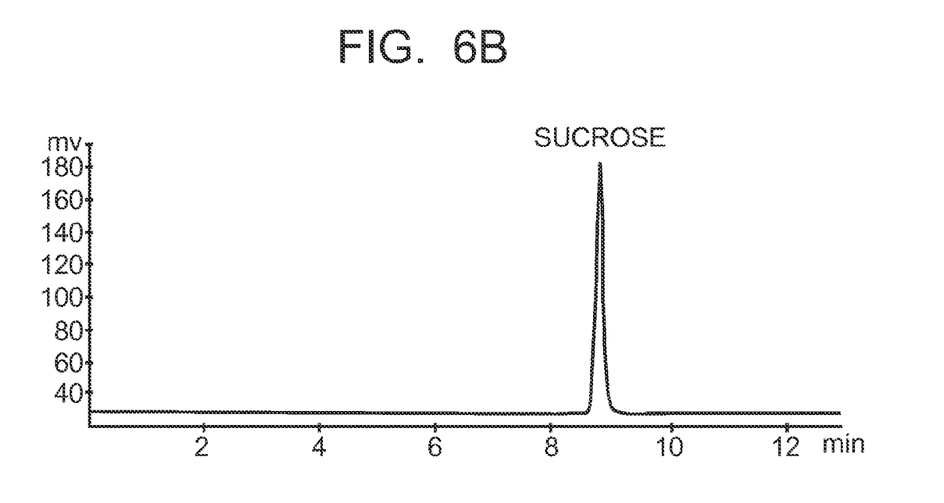

FIG. 6A shows a chromatogram of buffered lots#021708 at 1.25 years. FIG. 6B shows a chromatogram of freshly made lot (#022510) using a buffer. Both lots were stored at 25° C. Note that the >1 year old lot (#021708) showed no signs of sucrose degradation. The differences in the sucrose retention times between the 2 chromatograms of FIGS. 6A and 6B and compared to those in FIG. 5, are due to intentional alterations made in the mobile phase gradient in attempt to decrease the overall run time during HPLC method development. The differing retention times are not indications of change in the sucrose concentration. This was verified by running freshly prepared standards at each time point.

Applicants have discovered that the viscosity of an aqueous phase of a DDFPe/sucrose mixture extends the physical stability of the final emulsion such that the DDFP particles remain suspended and separated from each other for a longer period of time. Applicants have further discovered that the viscosity of an aqueous phase of a DDFPe/sucrose mixture decreases as a function of both the absence of a phosphate buffer species, and also as a function of a decreasing concentration of sucrose.

Figure 7:
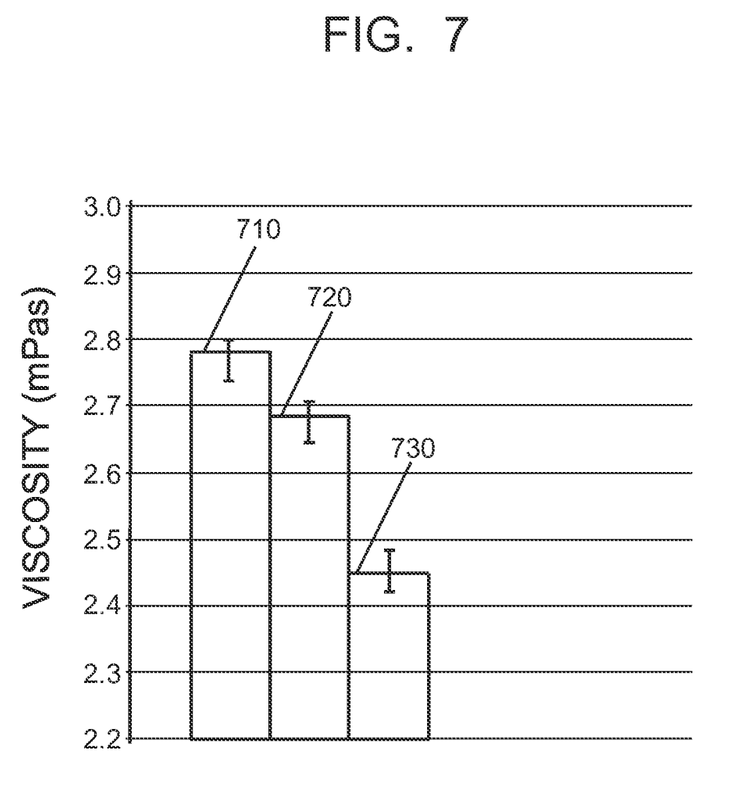
FIG. 7 depicts the viscosity comparison of the aqueous phase of DDFPe.

FIG. 7 graphically illustrates a viscosity comparison of the aqueous phase of NVX-108. Curve 710 shows the viscosity of a freshly made sucrose solution with a 0.01 M phosphate buffer. Curve 720 shows the viscosity of a freshly made 32% sucrose solution without any buffer. Curve 730 shows the concentration of a mixture comprising 18% sucrose, 7% fructose and 7% glucose without any buffer. The mixture of curve 730 corresponds to the breakdown of sucrose observed in NVX-108 lot#39588DK02 after 9 years.

Without pH adjustment and buffer capacity, the pH of DDFPe starts at about pH 4.5 to 5.5 and decreases with time. Acidic conditions promote the breakdown of the sucrose in DDFPe. In cases where the pH of the DDFPe sucrose solution was adjusted up to pH 7.2 and buffered there, a lack of sucrose breakdown was observed, while lots of DDFPe that were unbuffered showed notable sucrose breakdown as soon as 3 months after preparation. Addition of a phosphate buffer at 0.01 M concentration significantly improves the shelf life of the DDFPe formulation by maintaining the pH and discouraging the onset and subsequent acid catalyzed degradation of the sucrose. Maintaining the initial sucrose concentration, in turn, not only stabilizes the osmotic concentration but also provides the increased viscosity necessary to best stabilize the DDFP particles.

Sodium phosphate monbasic is the preferred buffer but a variety of other buffers including citric acid, citric acid monohydrate, dibasic calcium phosphate, edetate disodium, potassium acetate, potassium chloride, potassium citrate, potassium citrate tribasic monohydrate, potassium phosphate, sodium acetate, sodium bicarbonate, sodium chloride and trisodium citrate dehydrate may be employed in the invention. Generally the concentration of the buffer may range from about 0.001 M to about 1.0 M with a concentration of about 0.1 M most preferred.

In addition to sucrose, the preferred viscosity modifier in the invention, other disaccharides may be used including lactose, maltose, lactulose, trehalose, lactulose, cellobiose, kojibiose, nigerose, isomaltose, sophorose, laminaribiose, gentiobiose, turanose, maltulose, palatinose, gentiobiulose, mannobiose, melibiose, melibiulose, rutinose, rutinulose and xylobiose.

Other viscosity modifiers include hyaluronic acid, acacia, agar, alamic acid, alginic acid, aluminum monostearate, attapulite, bentonite, carbomers 910, 934, 934P, 940, 941, 1342 and carbomer copolymer, carbomer hompolymer, carbomer interpolymer, carboxymethylcellulose, carrageenan, cellulose, dextrin gelatin, gellan gum, hydroxyethyl cellulose, hydroxypropyl cellulose, hyproellose, magnesium aluminum silicate maltodextrin, methylcellulose, pectin, polyethylene oxide, polyethylene glycol, polyvinyl alcohol, povidone, propylene glycol alginate, silicon dioxide, sodium alginate, starch, tragacanth, gum arabic and xanthan gum.

A wide variety of materials can be used as fluorinated gases and/or fluorinated gaseous precursors for incorporating in or entrapping within stabilizing materials and vesicles. As described herein, the fluorinated gaseous precursors can be converted to a gas, by temperature or pressure, prior to administration to a patient. Exemplary fluorinated gases and fluorinated gaseous precursors for use in the present invention include, for example, hexafluoroacetone, 1,3-dichlorotetrafluoroacetone, tetrafluoroallene, boron trifluoride, 1,2,3-trichloro-2-fluoro-1,3-butadiene, hexafluoro-1,3-butadiene, 1-fluorobutane, perfluorobutane, decafluorobutane, perfluoro-1-butene, perfluoro-2-butene, 2-chloro-1,1,1,4,4,4-hexafluorobutyne, 2-chloro-1,1,1,4,4,4-hexafluoro-2-butene, perfluoro-2-butyne, octafluorocyclobutane, perfluorocyclobutene, perfluorocyclobutane, perfluorocyclopentane, octafluorocyclopentene, perfluorocyclopropane, 1,1,1-trifluorodiazoethane, hexafluorodimethylamine, perfluoroethane, perfluoropropane, perfluoropentane, hexafluoroethane, hexafluoropropylene, 1,1,2,2,3,3,4,4-octafluorobutane, 1,1,1,3,3-pentafluorobutane, octafluoropropane, octafluorocyclopentene, 1,1-dichlorofluoroethane, hexafluoro-2-butyne, octafluoro-2-butene, hexafluorobuta-1,3-diene, perfluorodimethylamine, 4-methyl-1,1,1,2-tetrafluoroethane, 1,1,1-trifluoroethane, 1,1,2,2-tetrafluoroethane, 1,1,2-trichloro-1,2,2-trifluoroethane, 1,1,1-trichloro-2,2,2-trifluoroethane, 1,1-dichloro-1,2-difluoroethylene, 1,1-dichloro-1,2,2,2-tetrafluoroethane, 1-chloro-1,1,2,2,2-pentafluoroethane, 1,1-difluoro-2-chloroethane, 1,1-dichloro-2-fluoroethane, dichloro-1,1,2,2-tetrafluoroethane, 1-chloro-1,1,2,2-tetrafluoroethane, 2-chloro-1,1-difluoroethane, 1,1,2-trifluoro-2-chloroethane, 1,2-difluorochloroethane, chloropentafluoroethane, dichlorotrifluoroethane, fluoroethane, nitropentafluoroethane, nitrosopentafluoroethane, perfluoroethylamine, 1,2-dichloro-2,2-difluoroethane, 1,1-dichloro-1, 2-difluoroethane, 1,2-dichloro-1,1,3-trifluoropropane, 1,2-difluoroethane, 1,2-difluoroethylene, trifluoromethanesulfonylchloride, trifluoromethanesulfenylchloride, (pentafluorothio)trifluoromethane, trifluoromethanesulfonylfluoride, bromodifluoronitrosomethane, bromofluoromethane, bromochlorodifluoromethane, bromochlorofluoromethane, bromotrifluoromethane, bromotrifluoroethane, chlorodifluoronitromethane, chlorofluoromethane, chlorotrifluoromethane, chlorodifluoromethane, dibromofluoromethane, dibromodifluoromethane, dichlorodifluoromethane, dichlorofluoromethane, 1-bromoperfluorobutane, difluoromethane, difluoroiodomethane, fluoromethane, perfluoromethane, iodotrifluoromethane, iodotrifluoroethylene, nitrotrifluoromethane, nitrosotrifluoromethane, tetrafluoromethane, trichlorofluoromethane, trifluoromethane, perfluoropent-1-ene, 1,1,1,2,2,3-hexafluoropropane, heptafluoropropane, 1,1,1,2,3,3,3-heptafluoropropane, 1,1,2,2,3,3,3-heptafluoropropane, 2,2-difluoropropane, heptafluoro-1-nitropropane, heptafluoro-1-nitrosopropane, heptafluoro-2-iodopropane, perfluoropropane, hexafluoropropane, 1,1,1,2,3,3-hexafluoro-2,3-dichloropropane, 1-bromo-1,1,2,3,3,3-hexafluoropropane, 1-bromoperfluoropropane, 2-chloropentafluoro-1,3-butadiene, 3-fluoropropane, 3-fluoropropylene, perfluoropropylene, perfluorotetrahydropyran, perfluoromethyltetrahydrofuran, perfluorobutylmethyl ether, perfluoromethyl-n-butyl ether, perfluoromethylisopropyl ether, perfluoromethyl-t-butyl ether, perfluorobutyl ethyl ether, perfluoromethylpentyl ether, 3,3,3-trifluoropropyne, 3-fluorostyrene, sulfur (di)-decafluoride ($S_2F_{10}$), sulfur hexafluoride, selenium hexafluoride, trifluoroacetonitrile, trifluoromethyl peroxide, trifluoromethyl sulfide, tungsten hexafluoride, 1-bromo-nonafluorobutane, 1-chloro-1-fluoro-1-bromomethane, 1-bromo-2,4-difluorobenzene, 2-iodo-1,1,1-trifluoroethane, bromine pentafluoride, perfluoro-2-methyl-2-pentene, 1,1,1,3,3-pentafluoropentane, 3-fluorobenzaldehyde, 2-fluoro-5-nitrotoluene, 3-fluorostyrene, 3,5-difluoroaniline, 2,2,2-trifluoroethylacrylate, 3-(trifluoromethoxy)-acetophenone, bis(perfluoroisopropyl)ether, bis(perfluoropropyl)ether, perfluoro isobutyl methyl ether, perfluoro n-propyl ethyl ether, perfluoro cyclobutyl methyl ether, perfluoro cyclopropyl ethyl ether, perfluoro isopropyl methyl ether, perfluoro n-propyl methyl ether, perfluorodiethyl ether, perfluoro cyclopropyl methyl ether, perfluoro methyl ethyl ether, perfluoro dimethyl ether and mixtures thereof.

Examples of various fluorinated compounds and their boiling points are set forth in a format as Compound/Boiling Point (.degree. C.) bromotrifluoroethane/−57.8; chlorotrifluoromethane/−81.5; dichlorodifluoromethane/−29.8; dibromofluoromethane/23; chloropentafluoroethane/−38.7; bromochlorodifluoromethane/−4; dichloro-1,1,2,2-tetrafluoroethane/3.1-3.6; octafluorocyclobutane/−5.8; decafluorobutane/−2; hexafluoroethane/−78.1; perfluoromethane/−129; perfluoroethane/−78.3; perfluoropropane/−36; perfluorobutane/−2; perfluoropropylene/−28; perfluorocyclobutane/−6; perfluoro-2-butyne/−25; perfluoro-2-butene/1.2; perfluorobuta-1,3-diene/6; perfluoro n-propyl ethyl ether/23.3; perflouro diethyl ether/3-4.5; perfluoro methyl ethyl ether/−23; perfluoro dimethyl ether/−59; sulfur hexafluoride/m.p. −50.5, sublimes −63.8; selenium hexafluoride/m.p. −34.6, sublimes −46.6; perfluoropropionyl chloride 8 1-bromo-1,1,2,3,3,3-hexafluoropropane/35.5; bromoperfluoropropane/35.5; 2-chloro-1,1,1,4,4,4-hexafluoro-2-butene/33; 2-chloropentafluoro-1,3-butadiene/37; iodotrifluoroethylene/30; 1,1,2-trifluoro-2-chloroethane/30; 1,2-difluorochloroethane/35.5; 1,1-difluoro-2-chloroethane 35.1 1,1-dichlorofluoroethane/31.8; 1-bromoethane/37; 1-fluorobutane 32.5 perfluoropentane/29.5; perfluorotetrahydropyran/34; perfluoromethyltetrahydrofuran/27; perfluoro t-butyl methyl ether/36; perfluoro n-butyl methyl ether/35.4; perfluoro isopropyl methyl ether/36; 1-bromo-nonafluorobutane/43; perfluorooctyliodide/160-161; perfluoroocytlbromide/142; 1-chloro-1-fluoro-1-bromomethane/38; 1,1,1-trichloro-2,2,2-trifluoro ethane/45.7; 1,2-dichloro-2,2-difluoro ethane/46; 1,1-dichloro-1,2-difluoro ethane/45; 1,2-dichloro-1,1,3-trifluoropropane/50.4;

1-bromoperfluorobutane/43; 1-bromo-2,4-difluorobenzene/44; 2-iodo-1,1,1-trifluoroethane/53 5; -bromovaleryl chloride/43; 1,3-dichlorotetrafluoroacetone/43; bromine pentafluoride/40.3; heptafluoro-2-iodopropane/39; 6-bromo-1-hexene/47; 2-bromo-2-nitropropane/45; 2-bromo-5-nitrothiophene/45; 2-bromopropene/47; 3-chloro-5,5-dimethyl-2-cyclohexene/44; 2-chloro-2-methylpropane/50; perfluoro-2-methyl-2-pentene/51; 1,1,1,3,3-pentafluoropentane/40; perfluorotributylamine/178; perfluorotripropylamine/130; 3-fluorobenzaldehyde/56; 2-fluoro-5-nitrotoluene/53; 3-fluorostyrene/40; 3,5-difluoroaniline/40; 2,2,2-trifluoroethylacrylate/45; 3-(trifluoromethoxy)-acetophenone/49; 1,1,2,2,3,3,4,4-octafluorobutane/44.8; 1,1,1,3,3-pentafluorobutane/40; perfluoro-4-methylquinolizidine/149; perfluoro-N-methyl-decahydroquinone/150-155; perfluoro-N-methyl-decahydroisoquinone/150-155; perfluoro-N-cyclohexyl-pyrrolidine/145-152; tetradecaperfluoroheptane/76; dodecaperfluorocyclohexane/52; n-perfluorohexane/59-60; perfluoroheptane/81; perfluorooctane/102; perfluorononane/125; perfluorodecane/about 143; perfluorododecane/m.p. 75-77; perfluoro-2-methyl-2-pentene/51; perfluorocyclohexane/52; peufluorodecalin/142; perfluorobutylethyl ether/60; bis(perfluoroisopropyl)ether/54; and bis(perfluoropropyl)ether/59.

Preferred gases and gaseous precursors are compounds which are sparingly soluble in water but which may, in some cases, be liposoluble, such as low molecular weight alkanes and their fluorinated analogs. Preferred gases and gaseous precursors include, for example, perfluorocarbons, perfluoroethers, and sulfur hexafluoride. Preferred perfluorocarbons may have from 1 to about 4 carbon atoms and from 4 to about 10 fluorine atoms. Preferred perfluoroethers have from 1 to about 4 carbon atoms, from 4 to about 10 fluorine atoms, and 1 to about 2 oxygen atoms, preferably 1 oxygen atom. Preferred gases and gaseous precursors for use in the present invention include perfluoromethane, perfluoroethane, perfluoropropane, perfluorobutane, perfluorocyclobutane, bromoperfluoropropane, perfluoropentane, perfluoroneopentane, perfluorocylcopentane, perfluorohexane, perfluoroheptane, perfluorooctane, perfluorononane, perfluorodecane, perfluoromethylbutyl ether ($CF_2$—O—$CF_2$ $CF_2$ $CF_2$ $CF_3$), perfluoromethyl-n-butyl ether, perfluoromethylisopropyl ether, perfluoromethyl-t-butyl ether, perfluorotetrahydropyran, perfluoromethyltetrahydrofuran, ($CF_3$ $CF_2$—O—$CF_2$ $CF_3$), perfluoromethylpentyl ether and other perfluoroether analogues containing between 4 and 6 carbon atoms, and optionally containing one halide ion, preferably $Br^{-1}$. For example, compounds having the structure $C_n F_y H_x OBr$, where n is an integer of from 1 to about 6, y is an integer of from 0 to about 13, and x is an integer of from 0 to about 13, are useful as gaseous precursors. Suitable gaseous precursors having this formula include perfluoropropyloxylbromide and 2-bromooxyperfluoropropane.

A fluorinated gaseous precursor and/or fluorinated liquid may be used in conjunction with the fluorinated gas of the present invention for administration to the patient. Whether the fluorinated compound is used as a liquid or a gas generally depends on its liquid/gas phase transition temperature, or boiling point. As known to one skilled in the art, the effective boiling point of a substance may be related to the pressure or temperature to which that substance is exposed. This relationship is exemplified by the ideal gas law: PV=nRT, where P is pressure, V is volume, n is moles of substance, R is the gas constant, and T is temperature. The ideal gas law indicates that as pressure increases, the effective boiling point increases also. Conversely, as pressure decreases, the effective boiling point decreases. When considering the PV=nRT equation, one skilled in the art will recognize that physiological pressures, especially inside arteries, may increase normal boiling points as much as about 5° C.

Preferably, the fluorinated gas used in the present invention is bromotrifluoroethane, chlorotrifluoromethane, dichlorodifluoromethane, dibromofluoromethane, chloropentafluoroethane, bromochlorodifluoromethane, dichloro-1,1,2,2-tetrafluoroethane, octafluorocyclobutane, decafluorobutane, hexafluoroethane, perfluoromethane, perfluoroethane, perfluoropropane, perfluorobutane, perfluoropropylene, perfluorocyclobutane, perfluoro-2-butyne, perfluoro-2-butene, perfluorobuta-1,3-diene, perfluoro n-propyl ethyl ether, perflouro diethyl ether, perfluoro methyl ethyl ether, perfluoro dimethyl ether, sulfur hexafluoride, selenium hexafluoride or perfluoropropionyl chloride. More preferably, the fluorinated gas is perfluoromethane, perfluoroethane, perfluoropropane, perfluorobutane, perfluorocyclobutane, perfluoro n-propyl ethyl ether, perflouro diethyl ether, perfluoro methyl ethyl ether, perfluoro dimethyl ether or sulfur hexafluoride. Even more preferably, the fluorinated gas is perfluoromethane, perfluoroethane, perfluoropropane or perfluorobutane. Most preferably, the fluorinated gas is perfluoropropane or perfluorobutane.

Preferably, the gaseous precursor, that has been converted to a gas, by temperature or pressure, prior to administration to a patient, is 1-bromo-1,1,2,3,3,3-hexafluoropropane, bromoperfluoropropane, 2-chloro-1,1,1,4,4,4-hexafluoro-2-butene, 2-chloropentafluoro-1,3-butadiene, iodotrifluoroethylene, 1,1,2-trifluoro-2-chloroethane, 1,2-difluorochloroethane, 1,1-difluoro-2-chloroethane, 1,1-dichlorofluoroethane, 1-bromoethane, 1-fluorobutane, perfluoropentane, perfluorotetrahydropyran, perfluoromethyltetrahydrofuran, perfluoro t-butyl methyl ether, perfluoro n-butyl methyl ether, perfluoro isopropyl methyl ether, 1-bromo-nonafluorobutane, 1-chloro-1-fluoro-1-bromomethane, 1,1,1-trichloro-2,2,2-trifluoroethane, 1,2-dichloro-2,2-difluoroethane, 1,1-dichloro-1,2-difluoroethane, 1,2-dichloro-1,1,3-trifluoropropane, 1-bromoperfluorobutane, 1-bromo-2,4-difluorobenzene, 2-iodo-1,1,1-trifluoroethane, 5-bromovaleryl chloride, 1,3-dichlorotetrafluoroacetone, bromine pentafluoride, heptafluoro-2-iodopropane, 6-bromo-1-hexene, 2-bromo-2-nitropropane, 2-bromo-5-nitrothiophene, 2-bromopropene, 3-chloro-5,5-dimethyl-2-cyclohexane, 2-chloro-2-methylpropane, perfluoro-2-methyl-2-pentene, 1,1,1,3,3-pentafluoropentane, 3-fluorobenzaldehyde, 2-fluoro-5-nitrotoluene, 3-fluorostyrene, 3,5-difluoroaniline, 2,2,2-trifluoroethylacrylate, 3-(trifluoromethoxy)-acetophenone, 1,1,2,2,3,3,4,4-octafluorobutane, 1,1,1,3,3-pentafluorobutane, tetradecaperfluoroheptane, dodecaperfluorocyclohexane, n-perfluorohexane, perfluoro-2-methyl-2-pentene, perfluorocyclohexane, perfluorobutylethyl ether, bis(perfluoroisopropyl) ether and/or bis(perfluoropropyl)ether. More preferably, the fluorinated gaseous precursor, that has been converted to a gas, by temperature or pressure, prior to administration to a patient, is bromoperfluoropropane, perfluoropentane, perfluorocyclopentane, perfluorobutyl methyl ether, perfluoromethyl n-butyl ether, perfluoromethyl isopropyl ether, perfluoromethyl t-butyl ether, perfluorotetrahydropyran and/or perfluoromethyltetrahydrofuran. Most preferably, the fluorinated gaseous precursor that has been converted to a gas is perfluoropentane. Preferred forms of perfluoropentane include n-perfluoropentane and perfluoroisopentane.

Mixtures of different types of gases, such as mixtures of oxygen, fluorinated gases, gaseous precursors and/or other types of gases, gaseous precursors and/or liquids, can also be used in the present invention. The compositions of the present invention may comprise, for example, air, noble gases, such as helium, rubidium hyperpolarized xenon, hyperpolarized argon, hyperpolarized helium, neon, argon, xenon, carbon dioxide, nitrogen, isopropyl acetylene, allene, 1,2-butadiene, 2,3-butadiene, 1,3-butadiene, 2-methyl-1,3-butadiene, butadiene, 2-methylbutane, 1-butene, 2-butene, 2-methyl-1-butene, 3-methyl-1-butene, 4-phenyl-3-butene-2-one, 2-methyl-1-butene-3-yne, butyl nitrate, 1-butyne, 2-butyne, 3-methyl-1-butyne, 2-bromobutyraldehyde, carbonyl sulfide, crotononitrile, cyclobutane, methylcyclobutane, cyclopropane, 3-chlorocyclo-pentene, dimethylamine, 1,2-dimethylcyclopropane, 1,1-dimethylcyclopropane, 1,2-dimethylcyclopropane, ethylcyclopropane, methylcyclopropane, diacetylene, 3-ethyl-3-methyl diaziridine, dimethylethylamine, bis(dimethylphosphine)amine, dimethyloxonium chloride, 2,3-dimethyl-2-norbomane, 1,3-dioxolane-2-one, 1,1-dichloroethane, 1,1-dichloroethylene, chloroethane, 1,1-dichloroethane, methane, chlorodinitromethane, iodomethane, disilanomethane, 2-methylbutane, methyl ether, methyl isopropyl ether, methyllactate, methylnitrite, methylsulfide, methyl vinyl ether, neon, neopentane, nitrogen, nitrous oxide, 1,2,3-nonadecanetricarboxylic acid 2-hydroxytrimethyl ester, 1-nonene-3-yne, 1,4-pentadiene, n-pentane, 4-amino-4-methylpentan-2-one, 1-pentene, 2-pentene (cis and trans), 3-bromopent-1-ene, 2-chloropropane, tetrachlorophthalic acid, 2,3,6-trimethyl-piperidine, propane, 1-chloropropane, 1-chloropropylene, chloropropylene-(trans), chloropropane-(trans), 2-chloropropylene, 2-aminopropane, 1,2-epoxypropane, propene, propyne, 2,4-diaminotoluene, vinyl acetylene, vinyl ether, ethyl vinyl ether, 5-bromovaleryl chloride, 1-bromoethane, 6-bromo-1-hexene, 2-bromo-2-nitropropane, 2-bromo-5-nitrothiophene, 2-bromopropene, 3-chloro-5,5-dimethyl-2-cyclohexene, 2-chloro-2-methylpropane and mixtures thereof.

In certain preferred embodiments, the gases, for example, oxygen and a perfluorocarbon gas, may be combined with a fluorinated liquid compound including, but not limited to, perfluorooctyliodide, perfluorooctylbromide, 1,2-dichloro-1,1,3-trifluoropropane, 2-iodo-1,1,1-trifluoroethane, 2-chloro-2-methylpropane, perfluoro-2-methyl-2-pentene, perfluorotributylamine, perfluorotripropylamine, 3-fluorobenzaldehyde, 2-fluoro-5-nitrotoluene, perfluoro-4-methylquinolizidine, perfluoro-N-methyl-decahydroquinone, perfluoro-N-methyl-decahydroisoquinone, perfluoro-N-cyclohexyl-pyrrolidine, tetradecaperfluoroheptane, dodecaperfluorocyclohexane, perfluorohexane, perfluoroheptane, perfluorooctane, perfluorononane, perfluorodecane, perfluorododecane, perfluoro-2-methyl-2-pentene, perfluorocyclohexane, perfluorodecalin, perfluorobutylethyl ether, bis(perfluoroisopropyl)ether and bis(perfluoropropyl)ether. Preferably, the fluorinated liquid compound is perfluorohexane, perfluoroheptane, perfluorooctane, perfluorononane, perfluorodecane, perfluorododecane, perfluorodecalin, perfluorooctyliodide, perfluorooctylbromide, perfluorotributylamine, perfluorotripropylamine, perfluorobutyl ethyl ether, bis(perfluoroisopropyl)ether or bis(perfluoropropyl)ether.

The preferred fluorocarbons useful as an oxygen therapeutic have a boiling point between about room temperature and about or near physiological temperature. The preferred fluorocarbon is perfluoropentane with perfluoroisopentane being particularly preferred. Other materials include n-perfluoropentane, perfluorobutane, perfluorocyclohexane (bp 59-60° C.), perfluoromethylcyclopentane (bp 48° C.), n-perfluorohexane (bp 58-60° C.), perfluorocyclopentane (bp 45° C.) and perfluorotryethylamine and perfluorotriethylamine.

In the foregoing, example the fluorocarbon material is stabilized with a surfactant, comprising a fluorosurfactant. As one skilled in the art would recognize, a variety of different surfactants may be used to stabilize the gaseous precursors. In addition to fluorosurfactants another preferred class of surfactants comprised phospholipids. Other preferred surfactants include fatty acids and sterols. Following is an example of preparation of an emulsion of DDFP using phospholipid.

The following examples are presented to further illustrate to persons skilled in the art how to make and use the invention. These examples are not intended as a limitation, however, upon the scope of the invention.

EXAMPLE II

Example of Preparation of Lipid Suspension of DDFP

A 100 mL volumetric flask was filled to its volumetric mark with water. The flask was emptied into a beaker which contained a stir bar, and beaker was marked at water's meniscus. 5 mL of glycerol and 80 mL of WFI was placed in beaker and placed on stirplate and heated to 55° C. for 15 minutes. 488 mg of NaCl, 234 mg of $NaH_2PO_4$ and 216 mg of $Na_2HPO_4$ were added to the glycerol/WFI mixture. This was stirred until salts were completely dissolved. In second beaker on second stir plate, 10 mL of propylene glycol was placed into the beaker. While stirring, propylene glycol was heated to 55° C. 114.24 mg of dipalmitoylphosphatidylcholine ("DPPC") (Avanti Polar Lipid cat#850355P) was added to propylene glycol while continuing to stir, allowing DPPC to dissipate completely. When DPPC was completely dissolved, 133.61 mg of dipalmitoylphosphatidylethanolamine with covalently linked poly(ethylene glycol) molecular mass 5000 ("DPPE-PEG 5K") (Avanti Polar Lipid cat#880200P) was added to propylene glycol and allowed to dissipate completely. When second lipid was dissolved, contents of beaker with propylene glycol and lipids were added to beaker with the salts, glycerol and WFI. Aliquots of the hot WFI mixture were used to rinse all the lipid mixture into the beaker. Sufficient quantity of WFI was added to reach the 100 mL mark and stirred for 30 minutes. The lipid mixture was removed from stir plate and pH checked, adjusting to 6.5±0.5 using 1M HCl and/or NaOH. The lipid mixture was cooled to room temperature. While mixture was cooling, chiller lines and tubing were attached to homogenizer and pressure vessel. Chiller was started and set to 4° C. Bags of ice were placed around homogenizer.

When lipid mixture was cooled, it was poured into homogenizer sample cylinder.

DDFP was removed from freezer, contained within frozen graduated cylinder. 2 mL of DDFP was measured out and immediately added to the homogenizer's sample cylinder.

The cylinder was sealed and homogenization begun at 14,000 psi. The mixture was allowed to circulate for 30 minutes. The homogenizer was stopped and the flow directed from homogenizer to pressure vessel. The pressure vessel was vented. The homogenizer was restarted and all of the emulsion transferred to the pressure vessel. The homogenizer was stopped and the vent closed and the 3-way valve closed. The tubing was removed and the pressure vessel transferred to the filling hood. The gas and filler tubing was connected to pressure vessel. The pump was primed and calibrated to disperse 7.5 mL using graduated cylinder and Erlenmeyer flask. The vials were filled with DDFPe and immediately capped and crimped.

EXAMPLE III

A lipid suspension of DDFPe was prepared as above except that it was prepared in a 30% weight/volume sucrose solution yielding a viscosity of about 2.8 mPas. Two samples were prepared, one with a buffer at pH 7.0 using 0.01 M sodium phosphate and the other without a buffer. The sucrose broke down more quickly in the solution without a buffer and the amount of sucrose fell and the concentrations of glucose and fructose rose more quickly in the unbuffered suspension.

While the preferred embodiments of the present invention have been illustrated in detail, it should be apparent that modifications and adaptations to those embodiments may occur to one skilled in the art without departing from the scope of the present invention as set forth in the following claims.

We claim:

1. An oxygen therapeutic composition, consisting of:
water;
dodecafluoropentane;
sucrose;
sodium phosphate monobasic buffer;
wherein:
the buffer stabilizes a pH of the composition at between about 6.5 to about 7.5;
the composition comprises a viscosity of about 2.0 to about 3.5 mPas.

2. The composition of claim 1, wherein said sucrose is present at a level of between about 28 weight percent and about 30 weight percent.

3. The composition of claim 1, wherein said buffer is formed from equal molar parts of (0.005 M) $NaH_2PO_4$ and (0.005 M) $Na_2HPO_4$.

4. An oxygen therapeutic composition, consisting of:
water;
glycerol;
propylene glycol;
$NaH_2PO_4$;
$Na_2HPO_4$;
dodecafluoropentane;
dipalmitoylphosphatidylcholine; and
dipalmitoylphosphatidylethanolamine with covalently linked poly(ethylene glycol) molecular mass 5000.

5. The composition of claim 4, wherein said composition is homogenized to form an emulsion.

6. An oxygen therapeutic composition, consisting of:
water;
sucrose;
glycerol;
propylene glycol;
$NaH_2PO_4$;
$Na_2HPO_4$;
dodecafluoropentane;
dipalmitoylphosphatidylcholine; and
dipalmitoylphosphatidylethanolamine with covalently linked poly(ethylene glycol) molecular mass 5000.

* * * * *